(12) United States Patent
Lambert

(10) Patent No.: US 11,051,910 B2
(45) Date of Patent: Jul. 6, 2021

(54) MANDIBULAR REPOSITION DEVICE AND COUPLING THEREFOR

(71) Applicants: Geoffrey James Lambert, Greensborough (AU); Leanne Joy Lambert, Greensborough (AU)

(72) Inventor: Geoffrey James Lambert, Greensborough (AU)

(73) Assignees: Geoffrey James Lambert, Greensborough (AU); Leanne Joy Lambert, Greensborough (AU)

(*) Notice: Subject to any disclaimer, the term of this patent is extended or adjusted under 35 U.S.C. 154(b) by 600 days.

(21) Appl. No.: 15/558,134

(22) PCT Filed: Mar. 16, 2016

(86) PCT No.: PCT/AU2016/050183
§ 371 (c)(1),
(2) Date: Sep. 13, 2017

(87) PCT Pub. No.: WO2016/149742
PCT Pub. Date: Sep. 29, 2016

(65) Prior Publication Data
US 2018/0153643 A1    Jun. 7, 2018

(30) Foreign Application Priority Data

Mar. 20, 2015 (AU) ................. 2015901013
Nov. 19, 2015 (AU) ................. 2015101689

(51) Int. Cl.
*A61F 5/00* (2006.01)
*A61C 5/00* (2017.01)
*A61F 5/56* (2006.01)

(52) U.S. Cl.
CPC .............. *A61C 5/007* (2013.01); *A61F 5/566* (2013.01)

(58) Field of Classification Search
CPC .... A61C 5/14; A61C 7/08; A61C 7/36; A61F 5/37; A61F 5/56; A61F 5/566; A63B 71/085
(Continued)

(56) References Cited

U.S. PATENT DOCUMENTS 6,012,920 A    1/2000  Yoo
6,604,527 B1   8/2003  Palmisano
(Continued)

FOREIGN PATENT DOCUMENTS

AU    2006200882 A1    9/2006
ES       2389407 A1    10/2012
(Continued)

OTHER PUBLICATIONS

Australian Examination Repot No. 1 for corresponding Australian application No. 2016236827, dated Apr. 26, 2019.
(Continued)

*Primary Examiner* — Keri J Nelson
*Assistant Examiner* — Adam Baker
(74) *Attorney, Agent, or Firm* — Notaro, Michalos & Zaccaria P.C.

(57) ABSTRACT

An adjustable mandibular repositioning appliance including first and second connecting members and a link arm which is pivotable about an axis wherein protrusive positioning of the mandible is provided by relative positioning of the link arm along aid axis, to kits and couplings for making a readily adjustable mandibular appliance, to a system for providing a readily adjustable mandibular repositioning appliance and methods of use.

23 Claims, 16 Drawing Sheets

(58) Field of Classification Search
USPC .... 128/848, 859, 861, 862; 433/5–8, 19, 24, 433/140
See application file for complete search history.

(56) References Cited

U.S. PATENT DOCUMENTS

| | | |
|---|---|---|
| 6,908,469 B2 | 6/2005 | Sellers |
| 8,316,857 B2 * | 11/2012 | Thornton ................ A61F 5/566 128/846 |
| 2011/0311936 A1 | 12/2011 | Marie-Catherine |
| 2013/0081638 A1 | 4/2013 | Petelle et al. |
| 2013/0280670 A1 | 10/2013 | Edgren |
| 2014/0224257 A1 * | 8/2014 | Abramson ............. A61F 5/566 128/848 |
| 2014/0326253 A1 | 11/2014 | Baratier et al. |
| 2015/0216716 A1 * | 8/2015 | Anitua Aldecoa ....... A61C 7/08 128/848 |
| 2017/0000643 A1 * | 1/2017 | Gelb ...................... A61F 5/566 |

FOREIGN PATENT DOCUMENTS

| | | |
|---|---|---|
| KR | 200464664 Y1 | 1/2013 |
| WO | 2011/127893 A1 | 10/2011 |
| WO | 2015/118201 A1 | 8/2015 |

OTHER PUBLICATIONS

Australian Examination Report No. 2 for corresponding Australian application No. 2016236827, dated Jun. 14, 2019.
European Search Report for corresponding European patent application No. 16767519.8, dated Sep. 11, 2018.
International Search Report and Written Opinion of corresponding PCT Application No. PCT/AU2016/050183, dated Jun. 7, 2016.

* cited by examiner

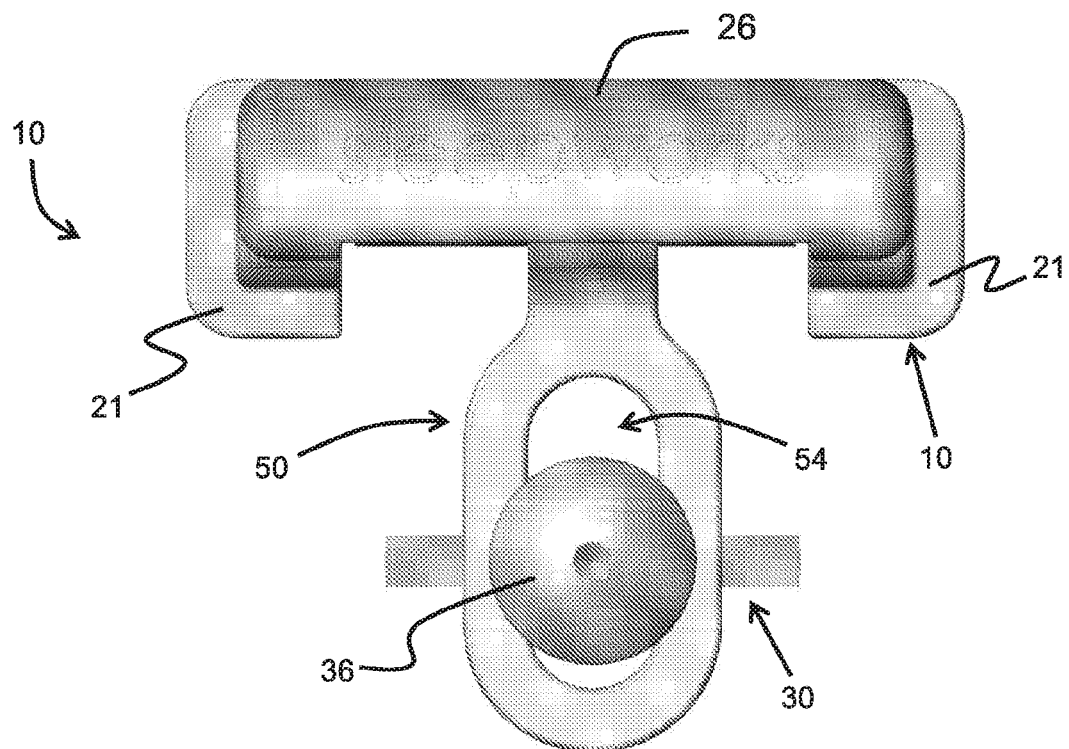
*Figure 3*
*Figure 4*
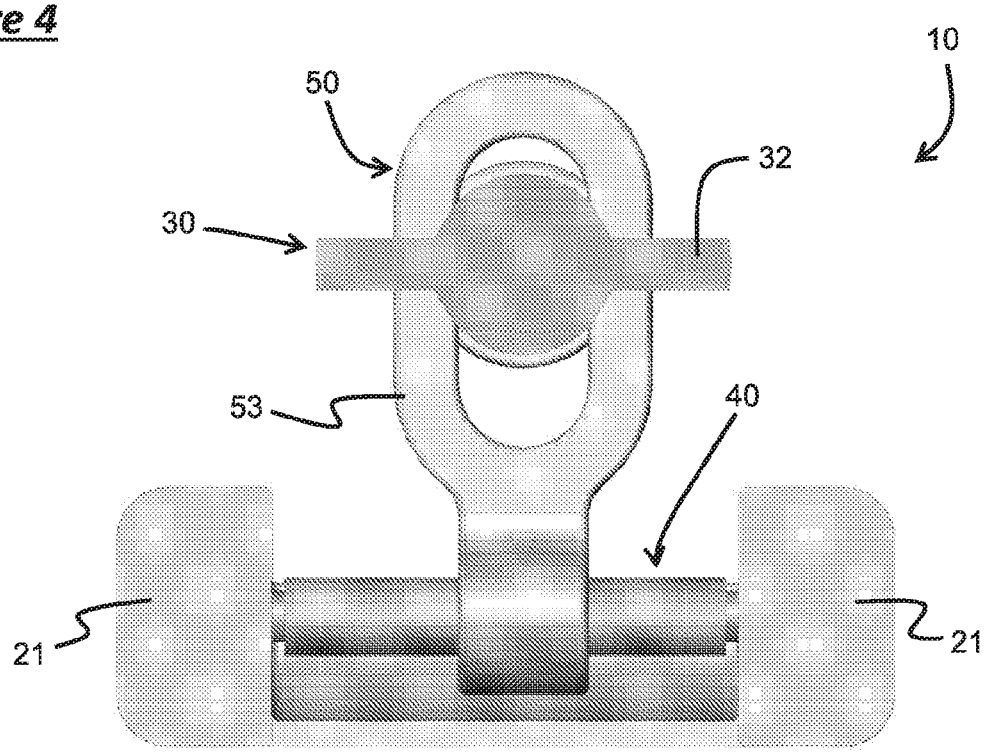

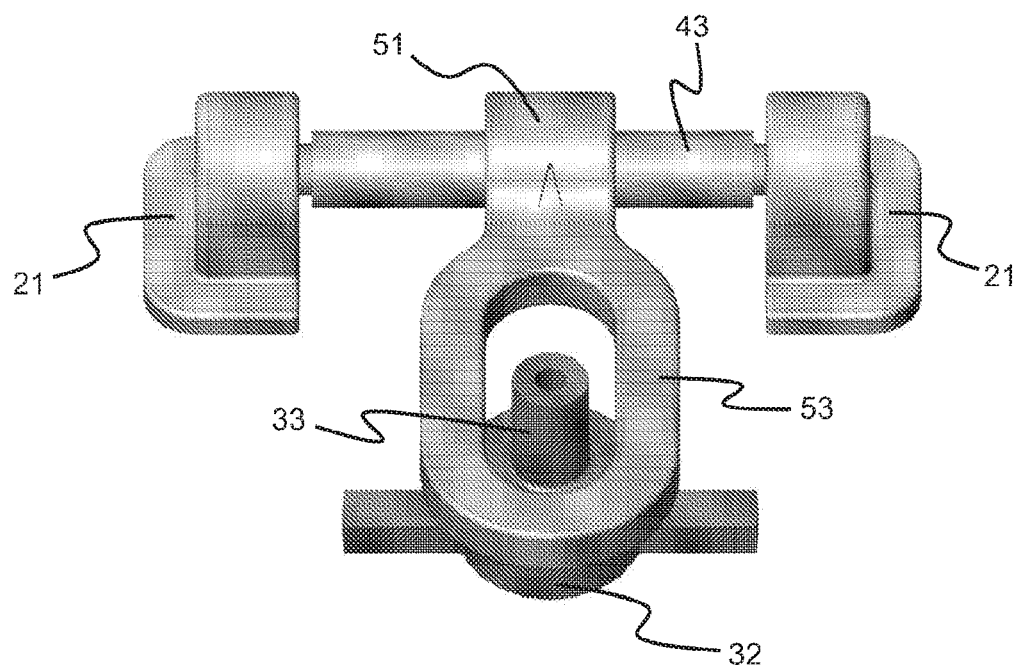
*Figure 5*
*Figure 6*
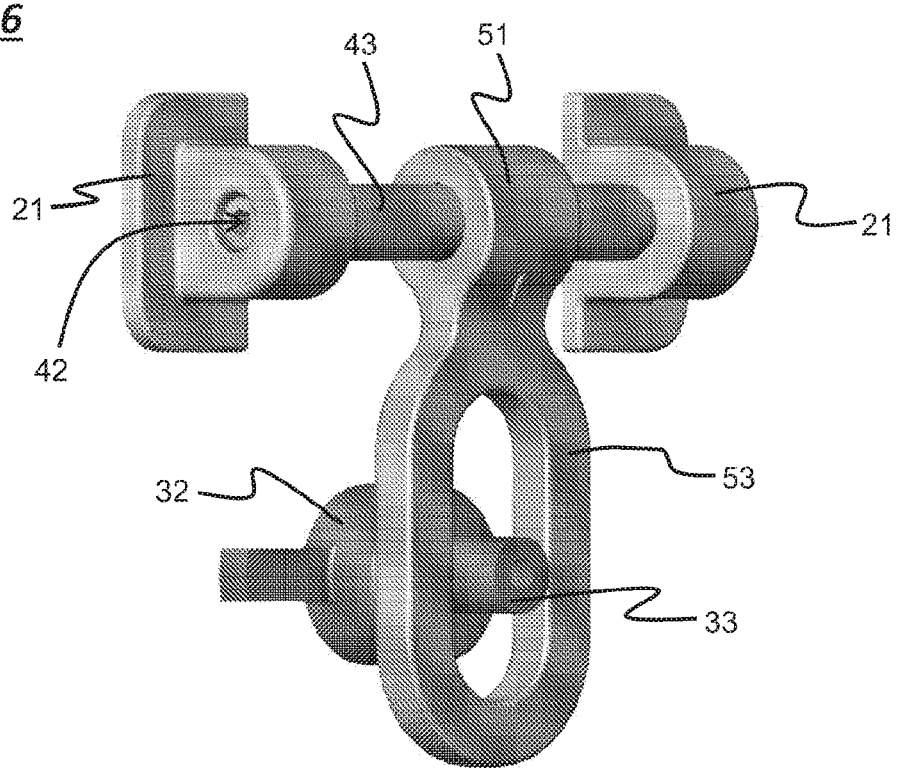

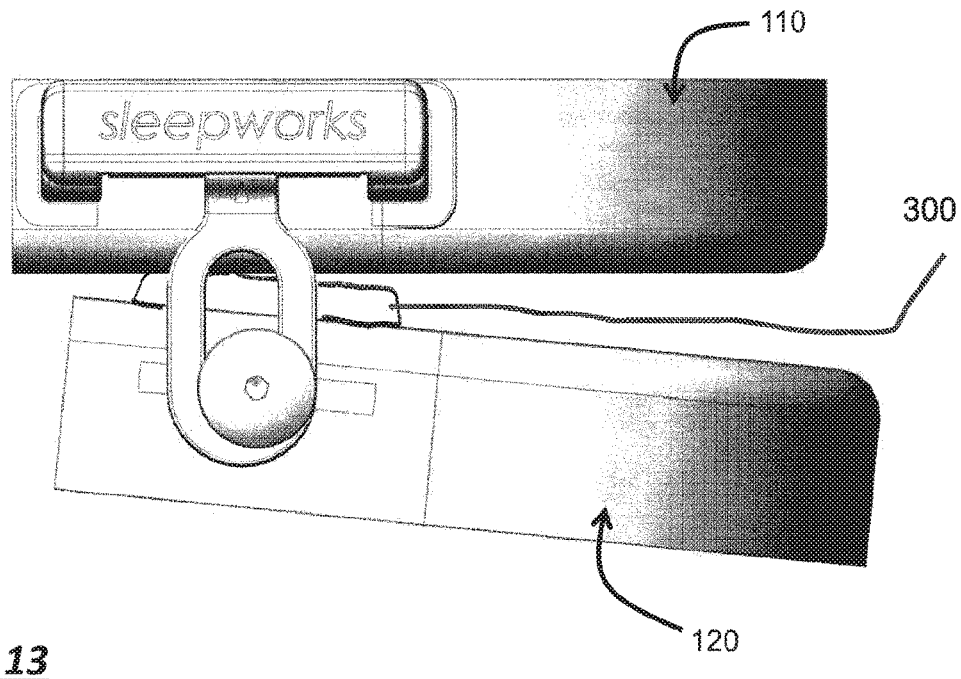
*Figure 13*
*Figure 14*
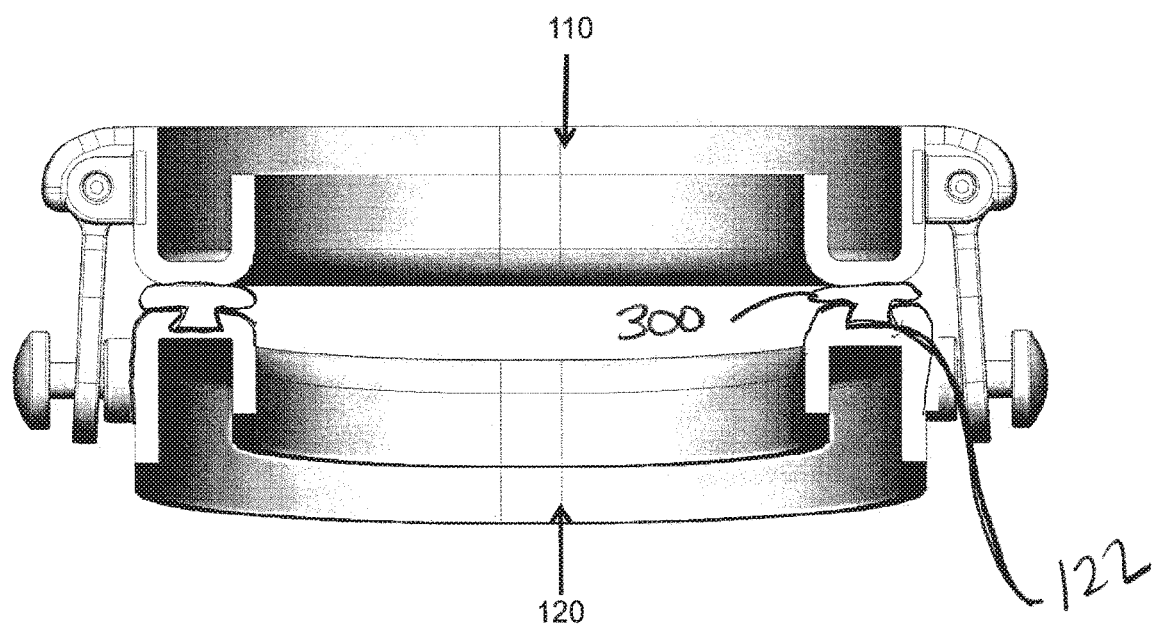

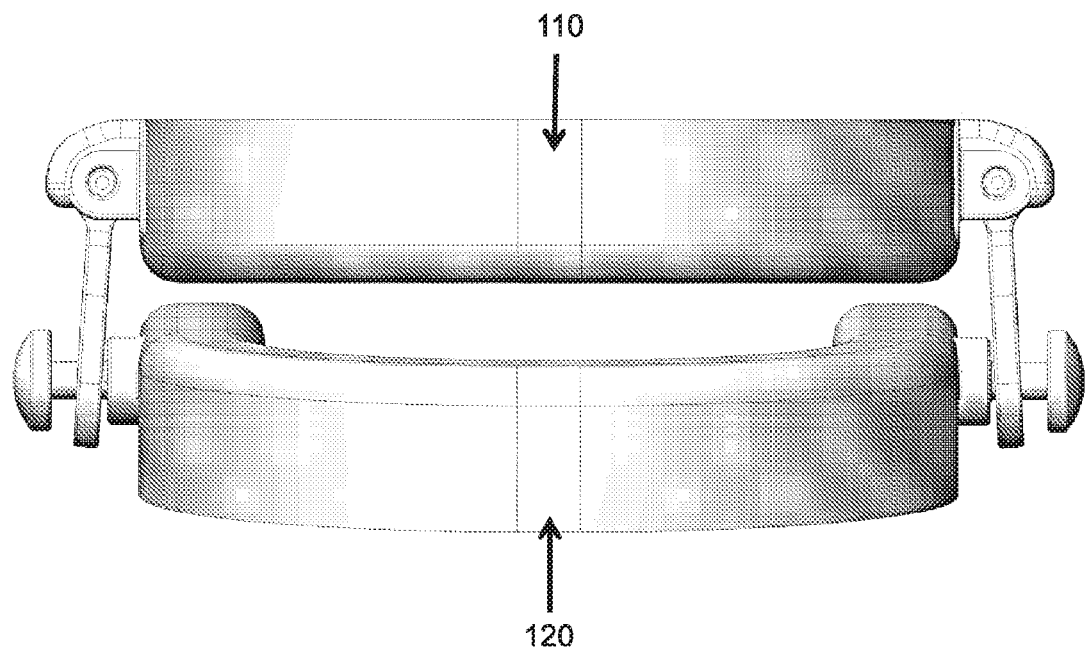
*Figure 15*
*Figure 16*
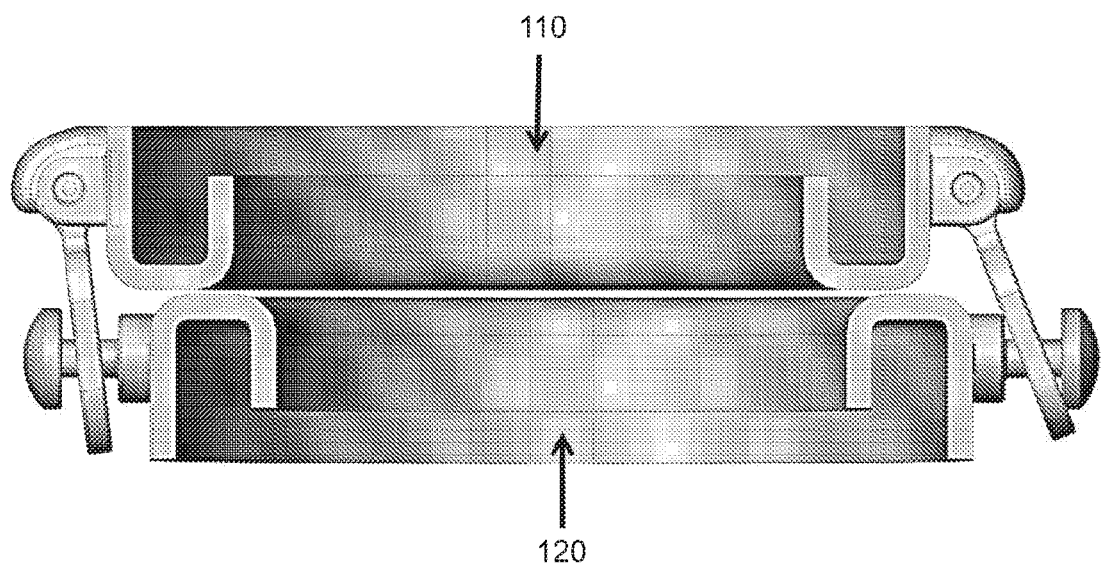

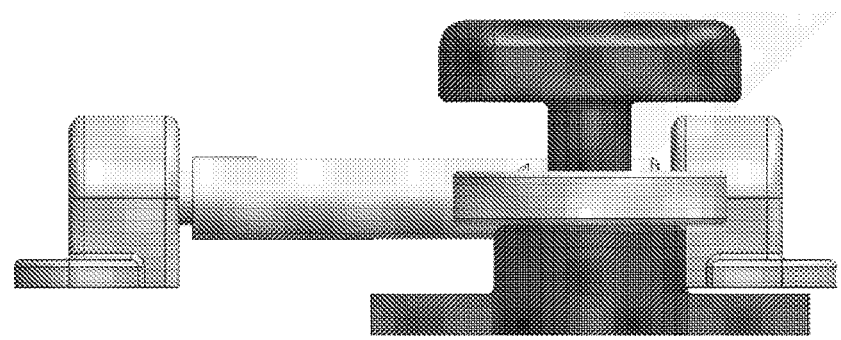
*Figure* 21
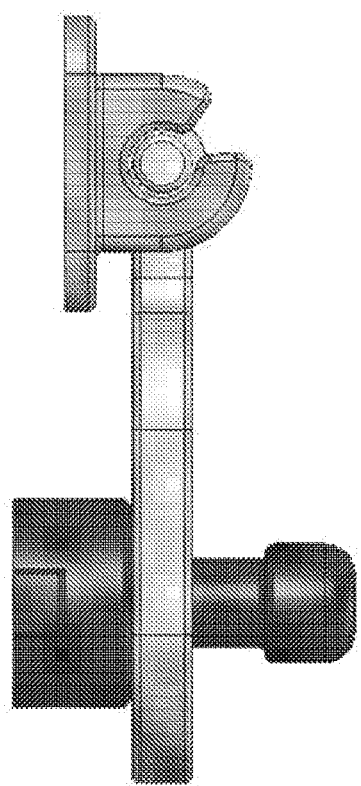
*Figure* 22

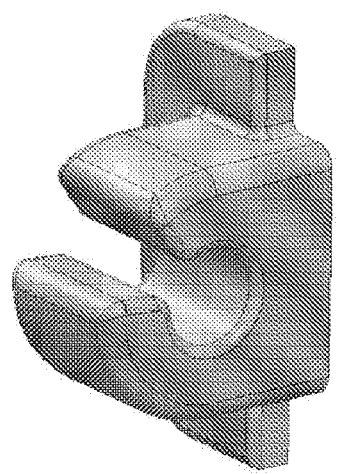
*Figure* 23
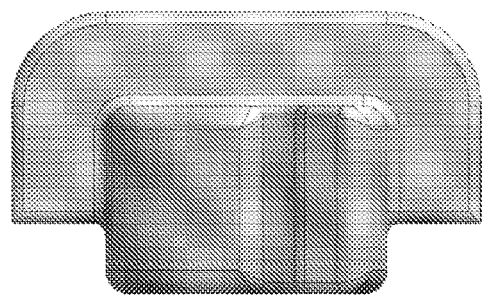
*Figure* 24
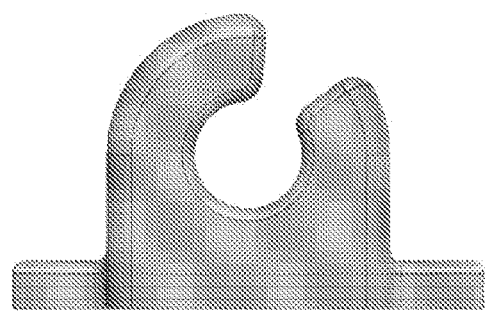
*Figure* 25

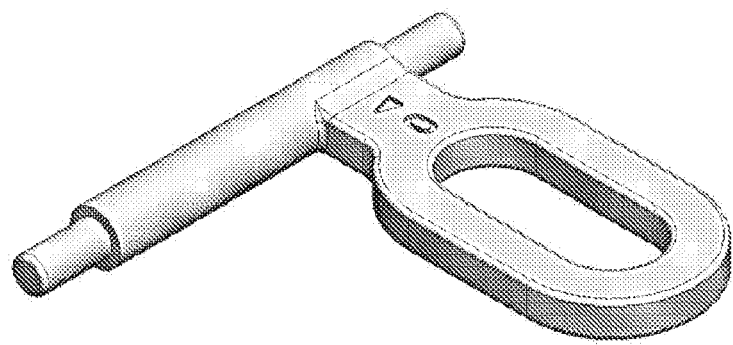
*Figure* 26
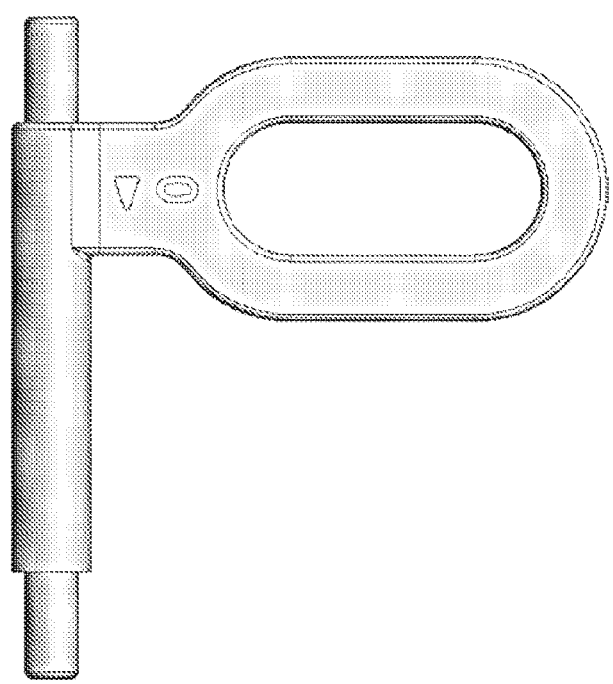
*Figure* 27

MANDIBULAR REPOSITION DEVICE AND COUPLING THEREFOR

FIELD OF INVENTION

The present invention relates to the field of medical devices, particularly dental devices.

In one form, the invention relates to mandibular repositioning devices and couplings for mandibular repositioning devices and the like.

It will be convenient to hereinafter describe the invention in relation to a mandibular repositioning device or mandibular advance splint that is useful for the treatment of snoring and/or obstructive sleep apnoea, however it should be appreciated that the present invention is not limited to that application only.

BACKGROUND ART

Sleep apnoea (or more correctly obstructive sleep apnoea) is a condition that affects about 5% of adults. Sleep apnoea can occur when the airway in the throat that leads from the nose and mouth to the lungs collapses when asleep and muscles are relaxed. If the collapse is severe enough it causes an apnoea (absence of breath). If it is a partial collapse it usually causes snoring. A person with severe sleep apnoea may have hundreds of these events each night which results in lack of oxygen to the body's vital organs and disrupted sleep. Long term consequences are high blood pressure and an increased risk of heart attack or stroke and, of course, sleepiness.

There are many treatments that have been tried for sleep apnoea but the treatment that is most effective, controlling the symptoms in almost everyone who uses it effectively, is Continuous Positive Airway Pressure (CPAP). Unfortunately a number of people with sleep apnoea do not tolerate CPAP and turn to other treatments such as surgery to the airway or an oral appliance.

Oral appliances are also called mandibular advancement splints (MAS) or mandibular advancement devices (MAD) and there are many types, not all of which are equally effective. The usual oral appliance consists of a "mouth guard" fitted to both the top teeth and the bottom teeth and then joined together in such a way that the bottom teeth are positioned slightly forward of the top teeth. Pushing the bottom jaw forward in most people opens up the airway and supports it so that it is less likely to collapse, in this way helping to reduce either the number or severity of the apnoea events. For most people, advancing the jaw by about 8 to 10 mm is enough to make a difference but the optimum amount of advancement varies from person to person and for each individual may require adjustment to reach a setting that is both effective and tolerably comfortable.

A number of different forms of mandibular advancement devices are available or have been proposed, however known devices have not been without limitation. For example, Australian Patent 2006200882 discloses a dental device which fastens together the upper and lower dental splints at the front. When fastened the device is adjusted so that the lower splint is fixed in relation to the upper splint in order to appropriately reposition the mandible. However, when fastened the user is not permitted any substantial movement of the jaw, which can be disconcerting, uncomfortable and inconvenient for the user.

Another example of a mandibular advancement device can be seen in U.S. Pat. No. 6,604,527. In this form of device the upper and lower plates are provided with opposed flange protrusions with angled engagement surfaces. When the user's jaw is closed, the flange engagement surfaces bear against one another with the effect of advancing the lower (mandible) plate relative to the upper. However, once the mouth begins to open the effective mandibular repositioning is lost, and furthermore the device is not readily adjustable and/or does not provide an adequate range of adjustment. This form of device also does not permit the user any substantial degree of lateral jaw movement.

A further example of a mandibular advancement device is Spanish patent published as ES 2389407. This is similar to Australian Patent 2006200882 in as far as it discloses a device which fastens upper and lower dental splints ventrally over the central incisors. The device includes anterior flanges mounted in pockets which sit above the front teeth on the dental splints. These flanges are associated with a central screw mechanism which is advanced centrally in the mouth along the dorsal ventral axis of the patient to obtain the required mandibular displacement. The flanges are to some extent able to move in the pockets allowing some flexibility however the device includes a number of small fiddly parts making manufacture and adjustment of the device complex and relatively difficult.

In view of the foregoing, it is desired to address or ameliorate one or more disadvantages or limitations associated with the prior art, or to at least provide a useful alternative.

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

The present application claims priority from Australian provisional patent application 201 5901 01 3 and Australian innovation patent 2015101689, the specifications and drawings of which are herein incorporated by reference.

SUMMARY OF INVENTION

In one aspect the present invention provides a mandibular repositioning appliance including:
a first splint with a first connecting member comprising a forward facing axis for protrusive positioning of a mandible:
a second splint with a second connecting member; and
a link arm coupled to first connecting member for pivotal movement about said axis, the link arm extending transverse to said axis to engage with said second connecting member in a slidable coupling that allows a range of relative movement in said transverse dimension;
wherein protrusive positioning of the mandible is provided by relative positioning of the link arm along said axis; and
wherein said members are attached to lateral legs of said splints such that the forward facing axis is substantially aligned with either side of the mid-sagittal plane in use in a patient.

In another aspect the present invention provides system for providing a readily adjustable mandibular repositioning appliance, said system including:

upper and lower dental splints;

a first connecting member attachable to one of said splints having a forward facing axis for protrusive positioning of the mandible:

a second connecting member attachable to the other of said splints;

wherein said members are attachable to lateral legs of said splints such that the forward facing axis is substantially aligned with either side of the mid-sagittal plane in a patient; and a series of interchangeable link arms, each of said arms mountable on the first connecting member for pivotal movement about said axis such that the arm extends transverse to said axis and is engageable with said second connecting member in a slidable coupling that allows in use a range of relative movement in said transverse dimension;

wherein said link arms are positionable at varying points along the axis to provide in use variable protrusion of the mandible and/or said link arms are of varying length to provide in use variable opening and closing movement of the mandible.

In yet another aspect the present invention provides a kit for making a readily adjustable mandibular appliance said kit including:

upper and lower dental splints;

at least one first connecting member attachable to one of said splints having a forward facing axis for protrusive positioning of the mandible:

at least one second connecting member attachable to the other of said splints;

wherein said members are attachable to lateral legs of said splints and the forward facing axes are substantially alignable either side of mid-sagittal plane in use in a patient; and a series of interchangeable link arms, each of said arms coupleable to the first connecting member for pivotal movement about said axis such that the arm extends transverse to said axis and is engageable with said second connecting member in a slidable coupling that allows in use a range of relative movement in said transverse dimension;

wherein said link arms are positionable at varying points along the axis to provide variable protrusion of the mandible and/or said link arms are of varying length to provide variable opening and closing movement of the mandible in use.

In accordance with the present invention there is provided a coupling device for use with a dental appliance for mandibular repositioning, including:

a pivot mount adapted for lateral attachment to a first splint with a generally forward facing axis with respect to the user of the dental appliance when in use;

a fixed mount adapted for lateral attachment to a second splint of the dental appliance; and a link arm coupled to the pivot mount for pivotal movement about said axis, the link arm extending transverse to said axis to engage with said fixed mount in a slideable coupling that allows a range of relative movement in said transverse dimension.

In accordance with the present invention there is also provided a mandibular repositioning appliance, including:

a first splint with a first connecting member attached to a side thereof;

a second splint with a second connecting member attached to a side thereof; and a link arm coupled to the first connecting member for pivotal movement about a generally forward facing axis with respect to the appliance when in use, the link arm extending transverse to said axis to engage with said second connecting member in a slideable coupling that allows a range of relative movement in said transverse dimension.

The first and second splints are preferably maxillary and mandibular splints, respectively, wherein the pivotal coupling of the link arm permits a range of side-to-side relative movement of the mandibular splint when in use. Furthermore, the slideable coupling permits a range of open-and-close relative movement of the mandibular splint when in use. Meanwhile, the relative position of the mandibular splint in the axial dimension is substantially maintained by the coupling.

In accordance with one particular form of the present invention there is provided a coupling device for use with a dental appliance for mandibular repositioning, including:

a first connecting member supporting an elongate position adjustment member having an external screw thread formation such that the position adjustment member is able to freely rotate about its elongate axis;

a second connecting member having a projecting flange formation; and a coupling link member having a through-hole with an internal screw thread formation to engage with the positioning adjustment member, and a coupling bar with a slot formation extending transverse to the axis of the through-hole for engagement with the projecting flange of the second connecting member wherein said first and second connecting members are suitable for lateral attachment to a splint to provide forward movement of a patient's mandible in use.

In accordance with the present invention there is also provided a device for coupling first and second splints in a mandibular repositioning appliance, including:

a first connecting member in use attached to the first splint;

an elongate position adjustment member having an external screw thread formation, supported for rotation about its elongate axis by the first connecting member;

a second connecting member in use attached to the second splint, the second connecting member having a projecting flange formation; and a coupling link member having a through-hole with an internal screw thread formation to engage with the positioning adjustment member, and a coupling bar with a slot formation extending transverse to the axis of the through-hole for engagement with the projecting flange of the second connecting member.

The engagement between the projecting flange of the second connecting member and the coupling bar preferably allows movement of the projecting flange along the slot formation. Preferably the slot formation is curved at its ends to facilitate rotational movement.

The position adjustment member may be provided with a tool socket or head by use of which the position adjustment member may be rotated relative to the coupling link member to effect adjustment of the location of the coupling link member along the position adjustment member through action of the screw threaded engagement.

A mandibular repositioning appliance including a maxillary splint and a mandibular splint and a coupling device as defined above interconnecting the maxillary and mandibular splints. Preferably the mandibular repositioning device includes two coupling devices, one on each side thereof. The first connecting member of the coupling device is attached to a side of the maxillary splint with the position adjustment member extending along the side. The second connecting member is attached to the side of the mandibular splint with the flange formation protruding laterally.

In accordance with the present invention there is also provided a mandibular repositioning appliance, including:
 a first splint with a first connecting member attached to a side thereof;
 an elongate position adjustment member having an external screw thread formation, supported for rotation about its elongate axis by the first connecting member;
 a second splint with a second connecting member attached to a side thereof, the second connecting member having a laterally protruding flange formation; and
 a coupling link member having a through-hole with an internal screw thread formation to engage with the positioning adjustment member, and a coupling bar with a slot formation extending transverse to the axis of the through-hole for engagement with the projecting flange of the second connecting member.

The appliance according to embodiments of the invention may be used to alleviate snoring, sleep apnoea and other sleep disorders; to alleviate certain types of temporal mandibular dysfunction or in temporal mandibular joint pain treatment; for orthodontic treatment; in post pharyngeal operations and examinations; or to retain the mandible in a forward opening position for other therapeutic purposes.

Specifically the present invention is directed to the use of the coupling device; device for coupling first and second splints in a mandibular repositioning appliance or the mandibular repositioning appliance:
 (i) to treat; alleviate and/or prevent snoring, sleep apnoea and other sleep disorders; certain types of temporal mandibular dysfunction or in temporal mandibular joint pain treatment;
 (ii) for orthodontic treatment;
 (iii) in post pharyngeal operations and examinations; or
 (iv) to retain the mandible in a forward opening position for other therapeutic purposes.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not limitative of the disclosure herein, and in which:

FIGS. 3 and 4 are plan and base views of the coupling mechanism, respectively;

FIGS. 5 and 6 are perspective views of the coupling mechanism with some components removed to reveal the underlying arrangement;

FIGS. 13, 14 and 15 are, respectively, side, rear and front views of the mandibular repositioning appliance illustrating an opening displacement capability;

FIG. 16 is a rear view of the mandibular repositioning appliance illustrating a sideways displacement capability;

FIGS. 21 and 22 are underside and front views, respectively, of the second embodiment coupling mechanism;

FIGS. 23 to 25 are various views of an attachment member from the second embodiment;

FIG. 26 is a perspective view of an integrated adjustment arm constructed according to the second embodiment;

FIG. 27 is a plan view of the integrated adjustment arm; and

FIG. 28 A shows an example of a longer adjustment arm.

DETAILED DESCRIPTION

A coupling mechanism constructed in accordance with an embodiment of the present invention is described hereinbelow, and illustrated in various views in FIGS. 1 to 8. The primary purpose of the coupling mechanism described is for use with a mandibular repositioning appliance (MRA), such as illustrated in various views in FIGS. 9 to 16.

Figure 1:
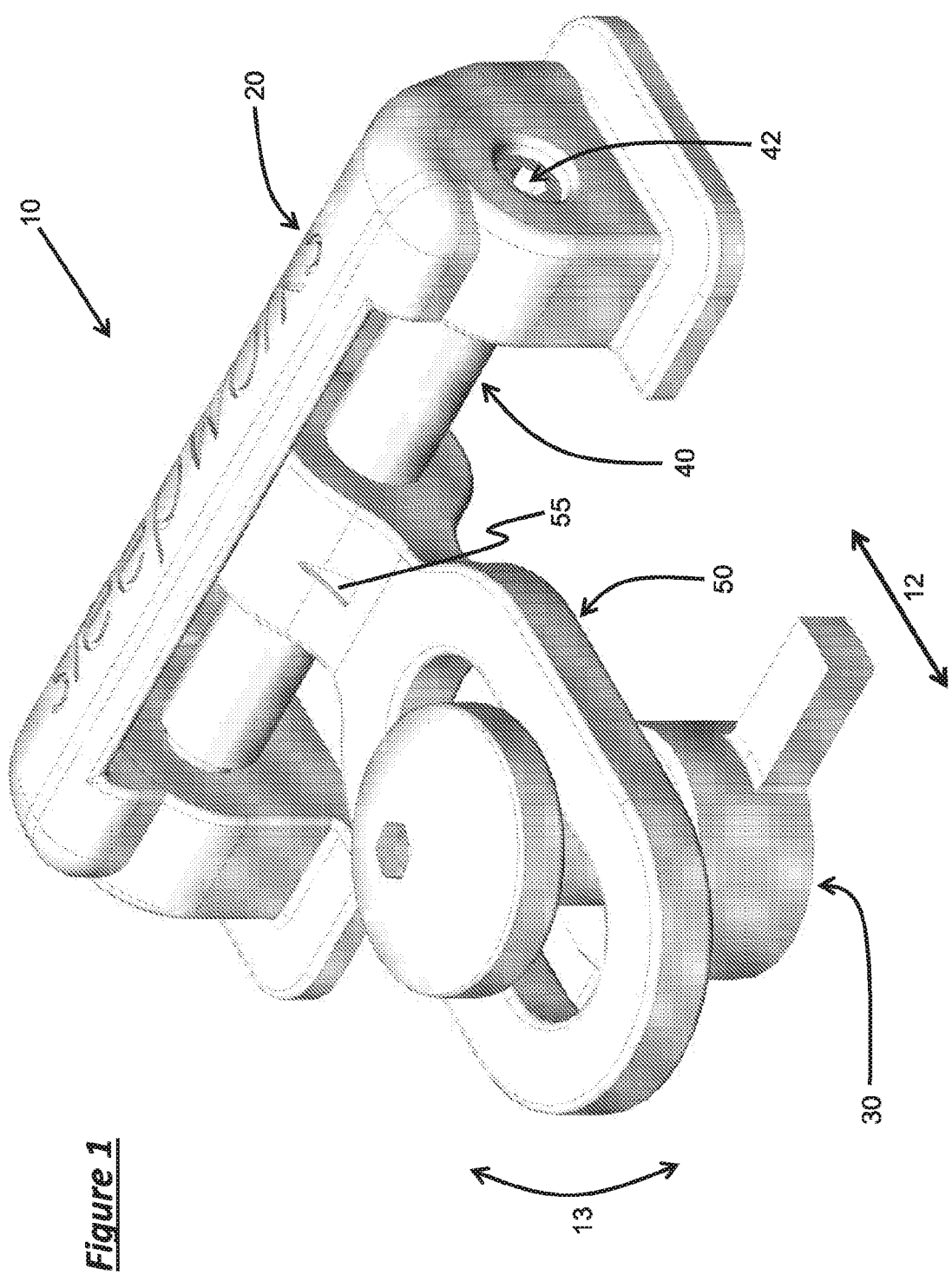
FIG. 1 is a perspective view of a coupling mechanism constructed in accordance with a first embodiment of the invention.

The coupling mechanism 10 is shown in perspective view in FIG. 1, from which the main mechanical features can be discerned. The coupling mechanism 10 includes a first attachment member 20 which is, in use, attached to one splint of an MRA, and a second attachment member 30, in use attached to the other MRA splint. The first and second attachment members are coupled to one another through a position adjustment member 40 and a positioning link arm 50.

The position adjustment member 40 is of elongate form and supported at each end by the first attachment member to be freely rotatable about its elongate axis. Between the ends supported by the first attachment member the position adjustment member is cylindrically shaped with an external screw thread formation (not detailed in the drawings for the sake of simplicity). The positioning link arm 50 has, at one end, a flange with a through-hole having an internal screw thread formation matching that of the position adjustment member. When assembled, as seen in FIG. 1, the position adjustment member extends through the positioning link arm through-hole secured by the respective screw thread formations. The location of the positioning link arm along the length of the position adjustment member can be altered by relative rotation of the position adjustment member, which function is described in greater detail below. The positioning link arm 50 projects perpendicularly to the position adjustment member axis and has a slot opening of lateral extent to said axis. The second attachment member 30 has a portion that extends through the slot opening and allows the second attachment member movement within the slot opening towards and away from the first attachment member 20.

Figure 2:
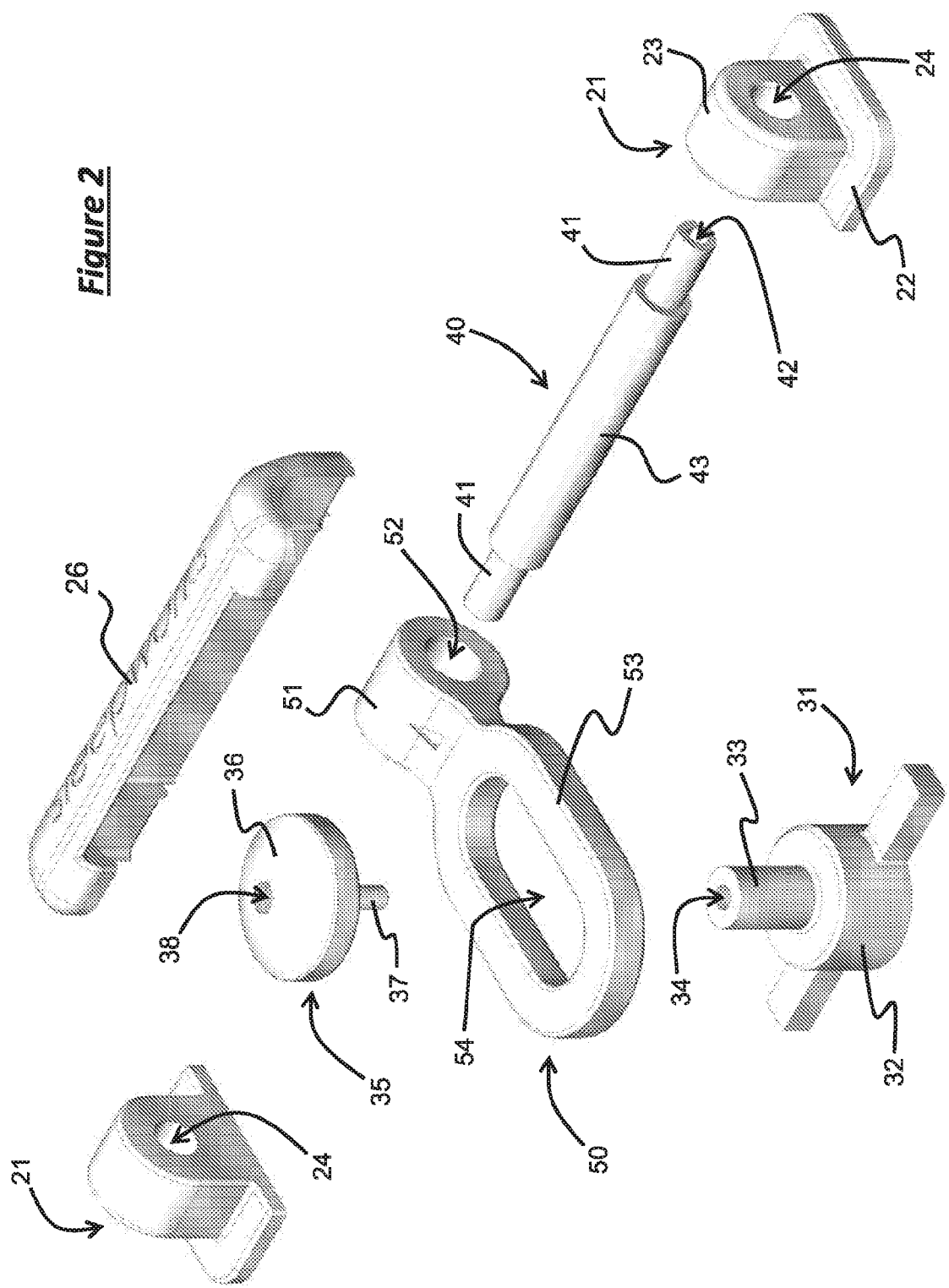
FIG. 2 is an exploded view of the coupling mechanism illustrating individual components of the first embodiment.

FIG. 2 shows the coupling mechanism components in an exploded view which enables the mechanism assembly to be explained. As shown, the first attachment member 20 is constructed from two end parts 21 and an interconnecting shield part 26. Each end part has a base 22 and an upstanding flange 23. Alternatively shield 226 and end parts 221 may be used in this embodiment (shield 226 and end part 221 are described later). Each end part flange 23 is formed with a bearing hole 24. When the first attachment member is in the assembled condition, the end parts 21 are positioned so that their bearing holes are coaxial to support the ends of the position adjustment member 40. The shield part 26 bridges between and interconnects the end parts 21, when assembled, leaving a gap between the end parts for access by the positioning link arm 50.

The position adjustment member 40 is an elongate and substantially cylindrical shaft. Each end of the position adjustment member has a portion 41 formed with a slightly smaller diameter than the screw threaded intermediate length. The end portions 41 are designed to fit into the bearing holes 24 of the first attachment member end parts 21 to allow free rotation of the position adjustment member about its axis. One or each end of the position adjustment member 40 is formed with a socket recess 42 for engagement with a hex-key or the like. The socket recess 42 is accessible within the bearing hole 24 when the coupling mechanism is in its assembled condition.

Figure 28:
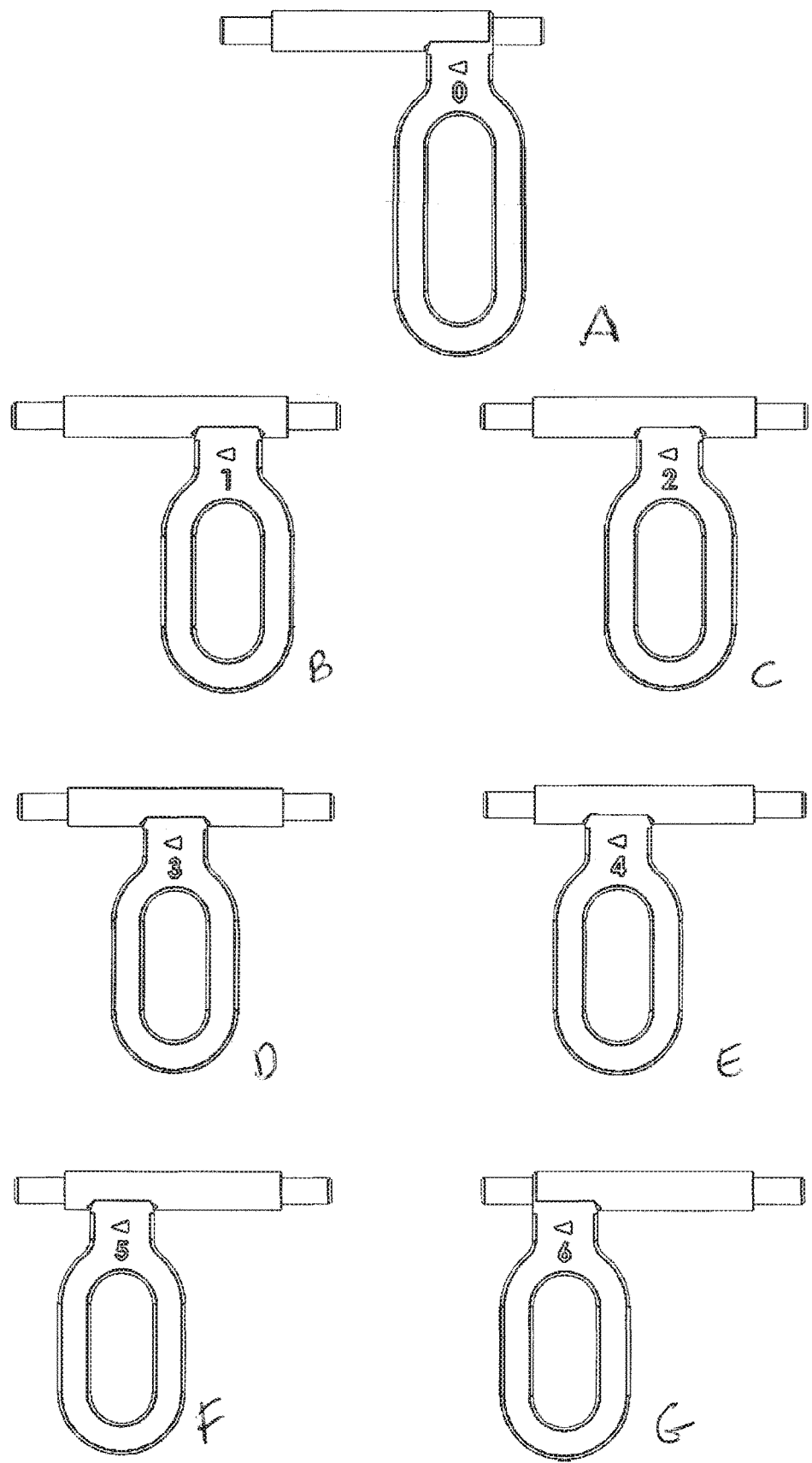
FIGS. 28 A to G are plan views of various integrated adjustment arms corresponding to different desired mandibular advancement amounts.

The positioning link arm 50 has an end flange 51 through which the internally screw-threaded through-hole 52 extends. Link arm 50 may be of varying lengths as shown in FIG. 28 A. An arm portion 53 projects radially with respect to the through-hole, and is formed with slot opening 54 of extent that is transverse to the through-hole axis. Slot opening 54 may have correspondingly different lengths and is curved at its ends to facilitate smooth rotational movement of spigot 31 described below.

The second attachment member is constructed in two parts: a spigot part 31 and a fastener part 35. The spigot part 31 has a base 32 and an upstanding spigot 33. The spigot may be of cylindrical form, for example, and has an internally screw-threaded hole 34 in its end distal to the base. The spigot 33 is of a size to allow it to extend through the slot opening 54 of the positioning link arm. The fastener part 35 is in the form of a bolt, for example, having a screw-threaded shaft 37 projecting from an enlarged head 36. The head 36 has a socket recess 38, coaxial with the shaft, for engagement by a hex-key or the like. The screw-threaded shaft of the fastener part is adapted to engage with the screw-threaded hole in the end of the spigot.

The coupling mechanism is assembled with the spigot 33 located in the slot opening 54 of the positioning link arm. The fastener part 35 is fastened to the end of the spigot so that the head 36 and base 32 are disposed at opposite sides of the arm portion 53, thereby retaining the spigot within the slot opening. This construction permits the second attachment member 30 to move relative to the first attachment member 20 within the extent of the spigot in the slot opening. The width of the slot opening is marginally larger than the diameter of the spigot so that movement of the second attachment member is relatively restricted in the direction parallel to the axis of the position adjustment member 40. The length of the spigot is somewhat greater than the thickness of the arm portion 53 so that there is a degree of freedom for movement of the second attachment member relative to the first attachment member in the circumferential sense of the position adjustment member.

The resulting coupling mechanism 10 is shown in various views in FIGS. 3, 4, 5 and 6. FIGS. 5 and 6 show the mechanism with the shield part 26 removed from the first attachment member and the fastener part 35 removed from the second attachment member, so that some aspects of the arrangement of components can be better seen in these drawings. The freedom of movement allowed whilst retaining protrusive positioning in a controlled manner significantly reduces pressure on the anterior teeth from the splints thereby reducing tooth movement.

As outlined above, when the coupling mechanism is assembled (e.g. as seen in FIG. 1) there are several modes of relative free movement between the first and second attachment members. One is defined by the spigot 33 in the slot opening 54 which permits relative movement of the first and second attachment members toward and away from one another transverse to the position adjustment member (e.g. as indicated by arrow 12 in FIG. 1). This allows opening and closing movements of the mandible. Another is defined by rotation about the axis of the position adjustment member 40 which allows the positioning link arm and second attachment member to move circumferentially (e.g. as indicated by arrow 13 in FIG. 1).

Figure 7:
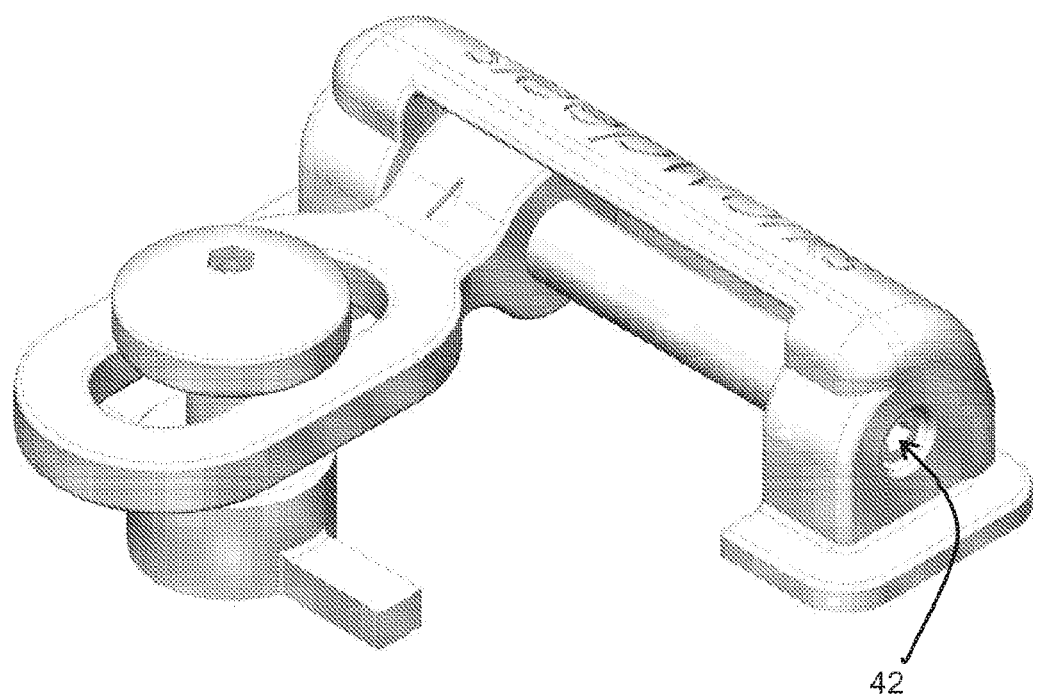
FIGS. 7 and 8 illustrate a range of adjustment of the coupling mechanism.
Figure 8:
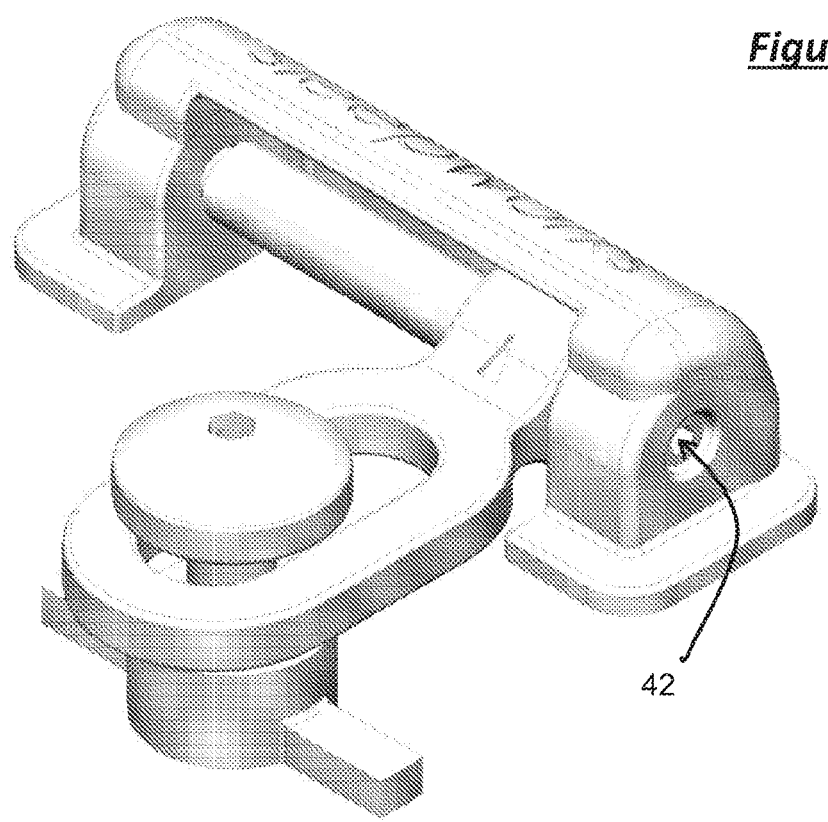
Figure 9:
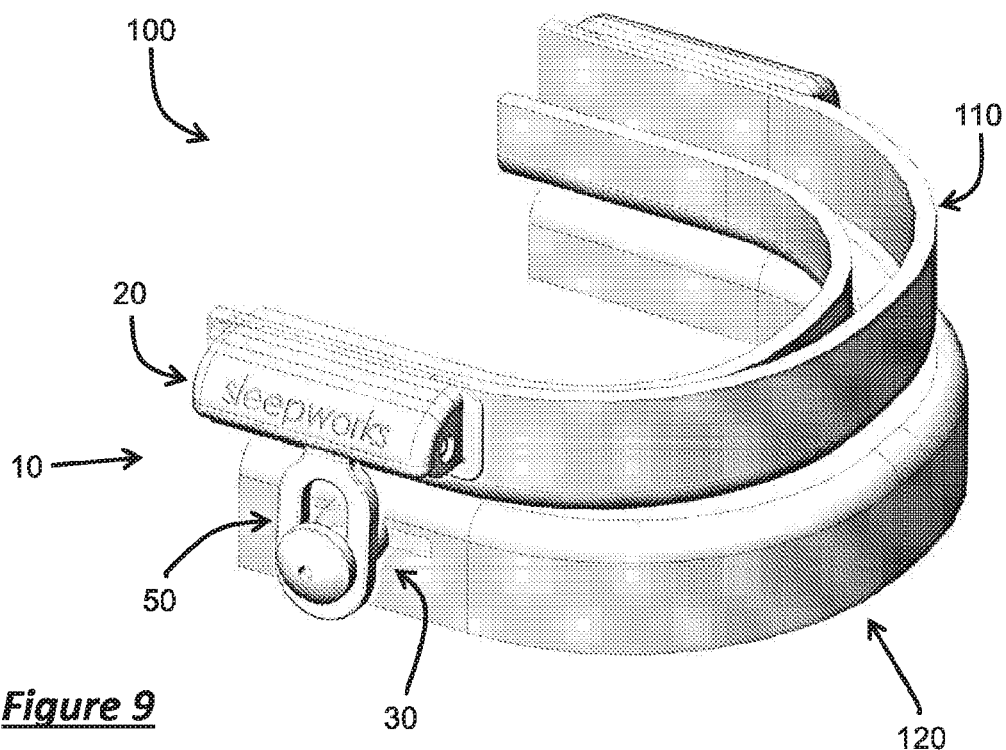
FIGS. 9 and 10 are front perspective views of a mandibular repositioning appliance incorporating a coupling mechanism in accordance with an embodiment of the invention.
Figure 10:
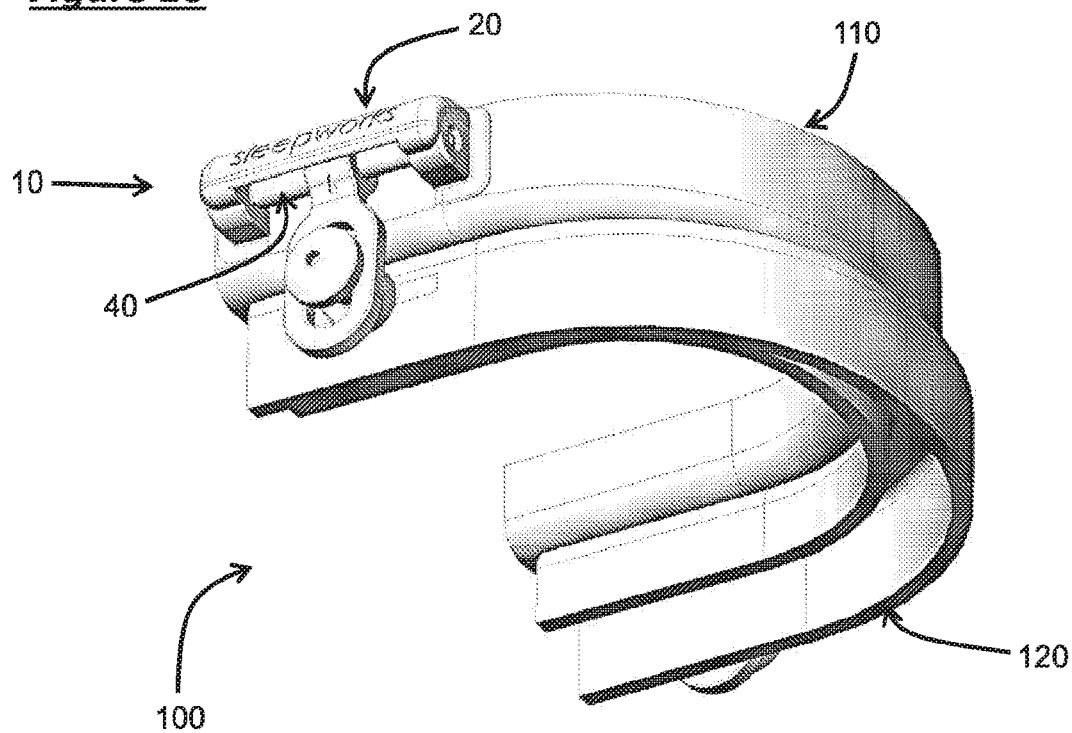
Figure 11:
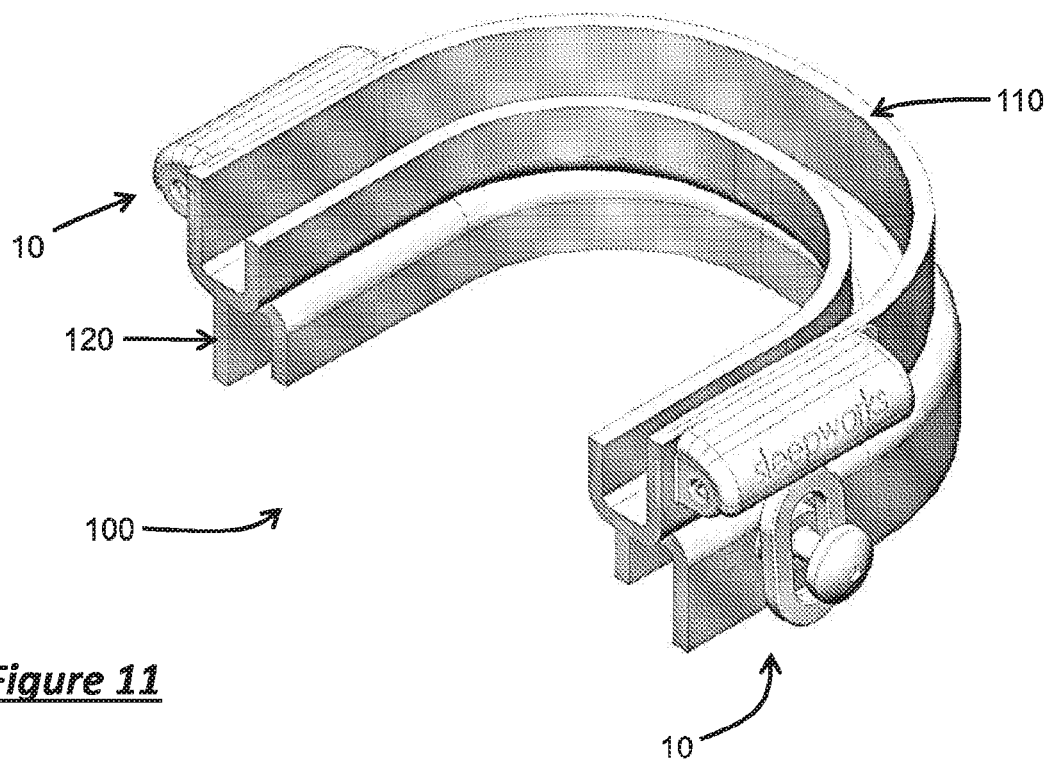
FIG. 11 is a rear perspective view of the mandibular repositioning appliance.

The main purpose of the coupling mechanism 10 is to provide coupling between upper (maxillary) and lower (mandibular) splints in an MRA. In general the idea is that, with the MRA fitted to the user, the splints promote relative forward advancement of the mandible which can assist in opening the user's airway. It is the coupling between the upper and lower splints that determines their relative positioning. Different users may require a different degree of mandibular advancement, so in order for the MRA to be applicable to a broad range of users the coupling mechanism is preferably adjustable to suit. FIGS. 7 and 8 illustrate an adjustment feature of the coupling mechanism 10.

When the coupling mechanism 10 is fitted to an MRA (described in greater detail hereinbelow), the first attachment member 20 is attached at a side of the upper splint, and the second attachment member 30 attached to the lower (mandibular) splint. When fitted, therefore, the position adjustment member 40 extends generally in the forward/backward direction relative to the user. Thus, adjustment of the location of the positioning link arm 50 along the length of the position adjustment member 40 can be used in practice to determine the amount of advancement of the mandibular splint relative to the maxillary splint. The adjustment can be accomplished by rotation of the position adjustment member relative to the positioning link arm through use of a hex-key in the end socket 42. Turning the position adjustment member in this way moves the positioning link arm along the position adjustment member by action of the screw-threaded engagement, whereby the pitch of the screw thread determines the amount of linear movement per rotation. A marker 55 (FIG. 1) on the positioning link arm may be provided for use with linear scale markings along the shield part 26 (not shown) to enable repeatable calibrated adjustment.

In FIG. 7 the coupling mechanism is shown at one end of its adjustment range, and in FIG. 8 the mechanism is shown at the other end of its range.

In FIGS. 9 to 16 a mandibular repositioning appliance (MRA) 100 is shown incorporating the coupling mechanism 10 according to an embodiment of the present invention. The MRA 100 has an upper (maxillary) splint 110 and a lower (mandibular) splint 120. The splints 110, 120 are generally moulded to fit around the upper and lower teeth, respectively, of a user. The structure of each splint may, for example, comprise a hard polymer (e.g. polycarbonate) outer shell portion and a softer polymer (e.g. polyurethane)

inner material that surrounds the user's teeth. In the drawings only the hard shell portion of the splints are shown for simplicity.

Each splint 110, 120 is U-shaped with generally parallel legs or sides joined by a curved front. The MRA 100 includes two coupling mechanisms 10, one for each side. This lateral placement of the couplings in the buccal vestibule provides uninterrupted airflow and allows greater potential oxygenation for a patient compared to devices which are located anteriorly. Further there is no restriction of the lingual/palatal anterior tongue space. The fact that there is no midline obstruction provides significant advantages.

In FIGS. 9, 10, 11 and 12 the coupling mechanism 10 disposed to the right-hand side of the MRA 100 is best seen. The first attachment member 20 is attached to the right-hand side of the upper splint 110, and the second attachment member 30 is attached to the right-hand side of the lower splint 120. The attachment members 20, 30 may be attached to the splints 110, 120 by moulding, adhesive bonding or other means. For example the attachment may be made by moulding the hard polymer material of the splint shell around the base of the attachment member thereby forming a unified structure.

Figure 12:
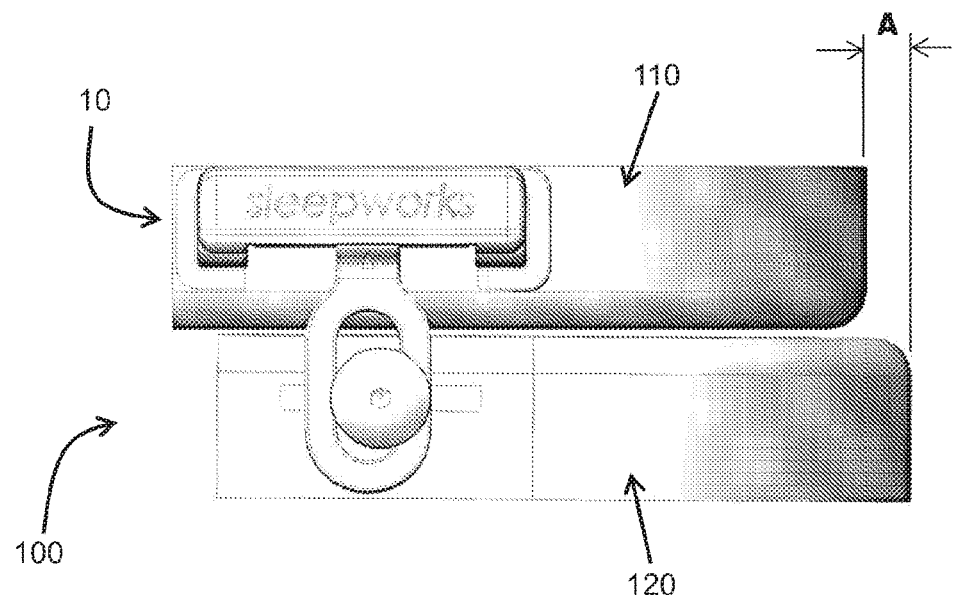
FIG. 12 is a side view of the mandibular repositioning appliance.
Figure 17A:
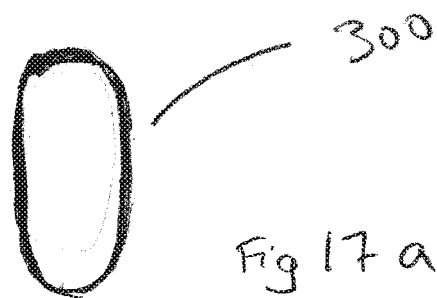
FIG. 17 is a top, side and end view of a bite pad for use in the mandibular repositioning appliance.
Figure 17B:
Figure 17C:
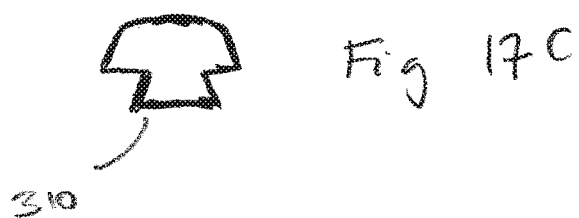
Figure 17:
Figure 18:
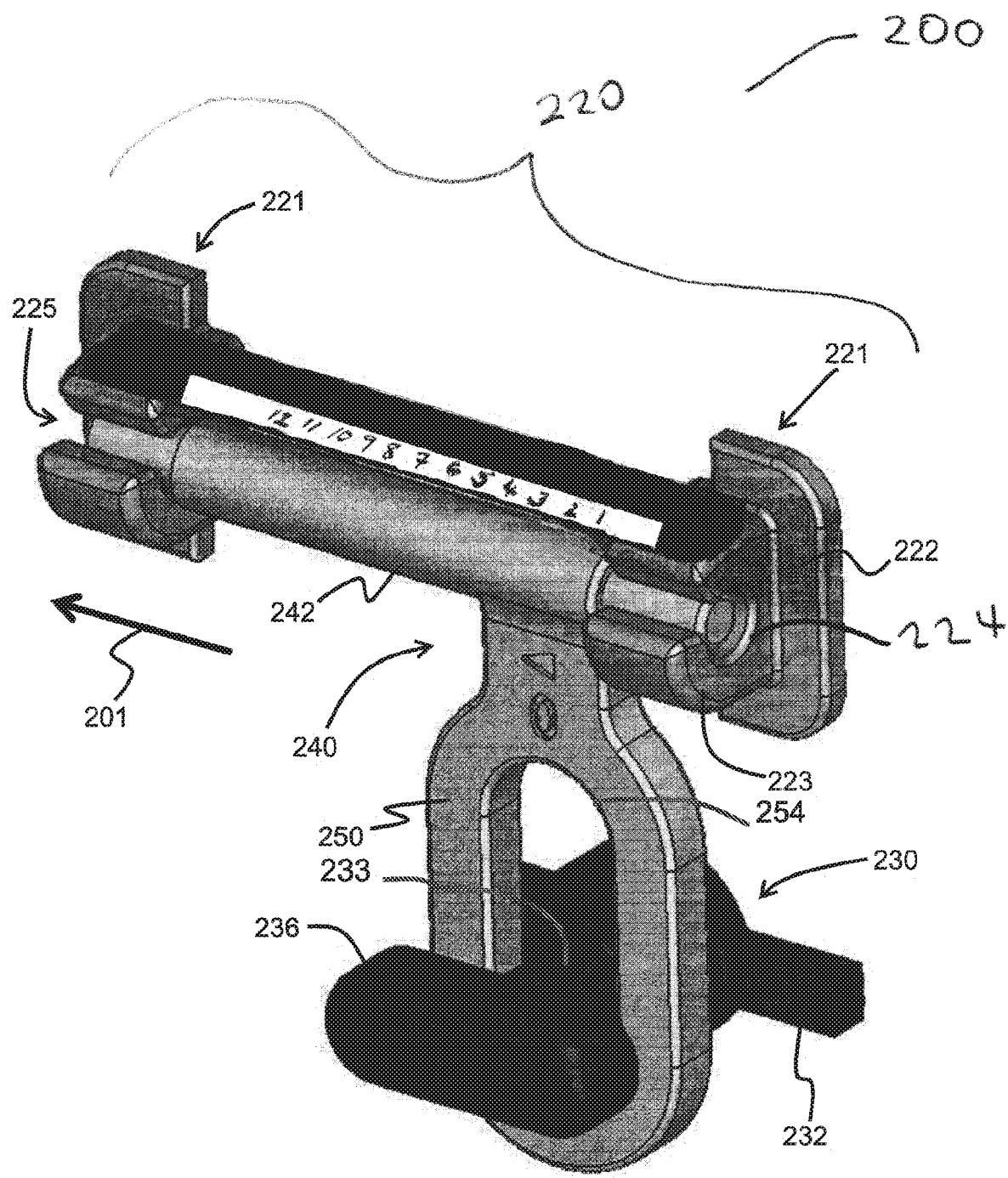
FIG. 18 is a perspective view of a coupling mechanism constructed in accordance with a second embodiment of the invention.
Figure 19:
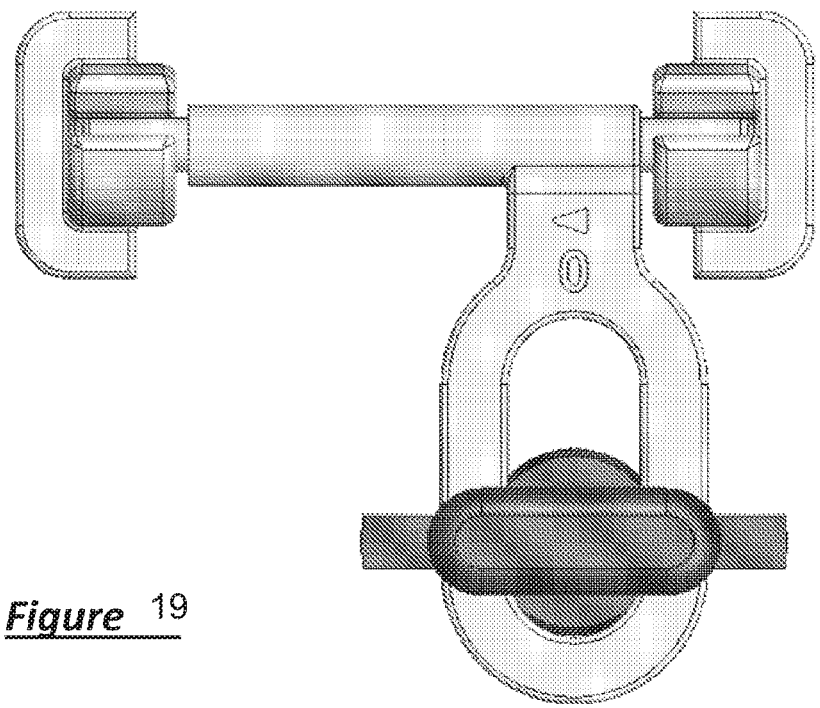
FIGS. 19 and 20 are plan and base views of the second embodiment coupling mechanism, respectively.
Figure 20:
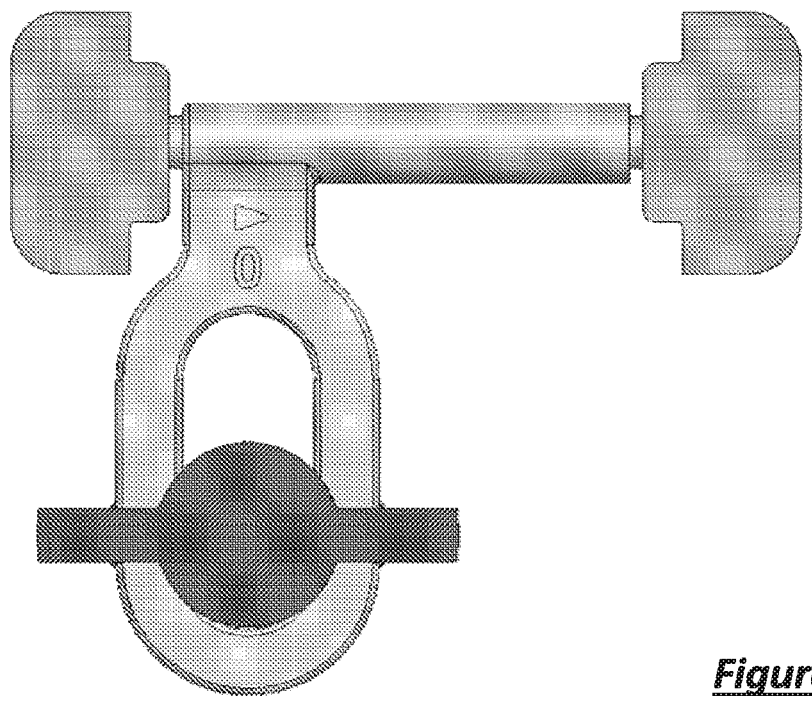

As shown, when the coupling mechanism 10 is attached in the MRA 100 the first attachment member 20 is mounted so that the position adjustment member 40 extends substantially parallel to the side of the upper splint 110 (i.e. substantially parallel to the mid-sagittal plane), and the second attachment member 30 is mounted so that the spigot 33 protrudes outwardly from the side of the lower splint 120. Alternatively attachment member 230 described later may be employed. The positioning link arm 50 mounted on the position adjustment member 40 extends down to its engagement with the spigot 33 in the slot opening 54. The forward/backward position of the lower splint is restricted by the engagement of the spigot in the slot opening, which can be adjusted as described above by adjusting the location of the positioning link arm along the position adjustment member. In FIG. 12, for example, the lower splint is shown advanced forward of the upper splint by an amount 'A'.

To provide for greater comfort and convenience of the user, the MRA 100 utilising the coupling mechanism 10 is designed to allow for some freedom of movement of the mandibular splint whilst still maintaining the desired repositioning (advancement). For example, FIGS. 13, 14 and 15 illustrate how the lower splint 120 of the MRA 100 can be moved in a manner that permits the user to open their mouth whilst still maintaining the desired mandibular advancement. This is enabled by the spigot and slot opening engagement that allows movement of the lower splint toward and away from the upper splint, vertically, whilst restricting the forward/backward movement.

The MRA 100 also permits the user sideways movement of the lower jaw by virtue of the coupling mechanism design. FIG. 16, for example, illustrates how coupling mechanism allows the lower splint to be displaced sideways relative to the upper splint. As well as greater comfort and convenience, allowing the user some lateral movement in this manner can also be beneficial to the tempo mandibular joint.

Optionally bite pad 300 may be used to provide greater comfort. Bite pad 300 is a lozenge shape member with tongue 310 on its underside. Bite pad 300 is secured in place by mating of tongue 310 with correspondingly shaped groove 122 in a top wall of lower splint 120 to form a dove tail joint. Bite pad 300 may be of varying height (for example from 1 to 5 mm) and different heights may be used on the left and right sides of MRA 100 as required. Posterior bite pads assist in relieving stress on the masticular and facial muscles while wearing the appliance.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

The coupling mechanism 10 may be constructed substantially from stainless steel, for example, as known for medical and dental devices. When assembled, the shield part 26 may be laser welded to the end parts 21. In order to ensure that the positioning link arm 50 is maintained in its desired location on the position adjustment member 40 without shifting during use, it is preferred that the screw-threaded engagement between these two components have substantially greater friction than that between the ends of the position adjustment member in the bearing holes. In other words, the position adjustment member 40 should be able to rotate relative to the first attachment member 20 much more easily than relative to the positioning link arm 50. For this reason, the positioning link arm 50 may be constructed from a different material, such as acetyl resin for example, that provides the increased friction with the screw thread of the adjustment member 40.

By way of example only, some relevant dimensions of the coupling device 10 are indicated below:
  Range of adjustment ~16 mm or 20 mm
  Diameter of position adjustment member ~3 mm
  Range of motion of spigot in slot opening ~5 mm
  Spigot length—link arm thickness ~4 mm A coupling mechanism according to a second embodiment of the invention is shown in FIGS. 18 to 28 and described below. The coupling mechanism 200 is shown in FIGS. 18 to 22 assembled but not incorporated with splints into a mandibular repositioning appliance. The coupling mechanism of the second embodiment has several structural differences in comparison with the first embodiment, but functions in fundamentally the same way as described above when in situ.

The coupling mechanism 200 has three primary components: a first attachment member 220, a second attachment member 230, and an integrated shaft and adjustment link arm 240. The first attachment member 220 is in use mounted to the upper splint of an MRA, and the second attachment member 230 mounted to the MRA lower splint. The arrow 201 shown in FIG. 18 corresponds to what would be the forward direction if the coupling mechanism were incorporated in an MRA. The coupling mechanism 200 shown in FIGS. 18 to 22 is adapted for use on the left-hand side of an MRA.

The first attachment member 220 comprises a pair of end parts 221 that are similar in structure to the end parts 21 of the first embodiment. An end part 221 is shown in various views in FIGS. 22 to 25. Each end part 221 has a base 222 and an upstanding flange 223. The base 222 is in use mounted to the side of the upper MRA splint. The flange 223 is formed with a bearing hole 224 and an axially aligned receiving slot 225. The end parts are bridged by shield 226 and are fixed in relation to one another. When so mounted, the two end parts are arranged with their bearing holes coaxially aligned and spaced apart. The two end parts 221 for one coupling mechanism 200 are actually formed as mirror images of one another, such that receiving slots 225 are also aligned when mounted in use.

The second attachment member 230 is generally similar in form to the attachment member 30 of the first embodiment, but is of unitary construction. The second attachment member 230 has a base 232 that is in use mounted to the outside of the MRA lower splint. Extending outwardly from the base is a spigot 233 on the end of which is an enlarged head formation 236. In this case the enlarged head 236 is formed integrally with the spigot, but is asymmetrically shaped.

The integrated adjustment link arm 240 provides the function of the position adjustment member shaft (40) and link arm (50) of the first embodiment, but is formed as a single structure. An adjustment link arm is shown in isolation in FIGS. 26 and 27. The adjustment link arm 240 has a cylindrical rod portion 242 with narrowed diameter sections 241 at each end adapted to fit into the bearing holes (224) of respective end parts of the first attachment member. Extending transversely from the rod 242 is an arm portion 250 with an elongate slot opening 254. The slot opening 254 is shaped to enable the spigot 233 of the second attachment member to extend therethrough, and is also dimensioned so that the enlarged head 236 can fit through the slot in one orientation but not the other. This enables the second attachment member to be engaged with the arm portion by rotating one with respect to the other through ninety degrees and inserting the head 236 through the slot 254.

One of the main differences between the coupling mechanism of the second embodiment and that of the first embodiment is the way in which the mechanism is adjusted to control the amount of mandibular advancement for a given user or from time to time. In the coupling mechanism 10 of the first embodiment the link arm 50 has a screw threaded engagement on the elongate position adjustment member shaft 40, whereby the position of the arm 50 along the member 40 can be adjusted by use of the screw thread. In coupling mechanism 200 of the second embodiment, however, the adjustment link arm 240 is integrally formed whereby the arm portion 250 is fixed with respect to the shaft or rod portion 242. Therefore, to provide for adjustment of mandibular advancement the coupling mechanism 200 employs a plurality of differently configured adjustment link arms 240 that can be readily interchanged. Seven adjustment link arm configurations are illustrated in FIGS. 28 A to G.

The purpose of the axially aligned slot in the first attachment member end parts 221 is to allow for the adjustment link arm 240 to be conveniently removed and replaced in the coupling mechanism 200. The end part 221 may be constructed from a polymer material, for example, that may be resiliently deformed to enable the rod portion end section 241 to snap-fit through open ended receiving slot 225 into the bearing hole 224, and to be similarly removed. Thus, to adjust the amount of mandibular advancement provided by the coupling mechanism one adjustment link arm can be removed from the mechanism and replaced by another of different configuration. As seen in FIG. 28, the various adjustment link arm configurations differ from one another by the position of the arm portion along the length of the rod portion. For example, the configuration shown in FIG. 28A corresponds to the minimum advancement amount, whilst the configuration of FIG. 28G represents the maximum advancement amount. In addition arm portion 250 may be of varying lengths with corresponding elongate slot openings 254 to provide more, or less vertical opening of the mandible as required (see FIG. 28 A).

In functional respects, when incorporated in an MRA and in situ, the coupling mechanism 200 performs in the same way as the mechanism 10. The mechanism is able to maintain a desired degree of mandibular advancement whilst still allowing some freedom of movement for the user to open their mouth and move their jaw from side to side. The coupling mechanism 200 has the advantage of being somewhat simpler in construction, although the trade-off is that the advancement distance is quantized rather than continuously variable as provided by the mechanism 10.

Since the coupling mechanism 200 does not involve a screw thread engagement it may be easier than the mechanism 10 to construct entirely from polymer materials. In fact the components of the coupling mechanism may be formed through any of a variety of processes known in the manufacturing arts. Injections moulding, for example, could be employed to form the components from suitable polymer materials, which process is particularly advantageous for the production of components in large numbers. Alternatively, components may be formed through the use of more recently developed manufacturing processes such as additive or subtractive manufacturing. Additive manufacturing, sometimes also referred to as 3D printing, is particularly useful for producing relatively small components on-demand without the need for specific and expensive production tooling. Regardless of the manufacturing technique, polymer materials used for the coupling mechanism components are preferably recognized for intra-oral biocompatibility and may include materials such as nylon (PA2200) or polycarbonate (PC-ISO). Those skilled in the art will recognize that various other and alternative materials may also be suitable.

The advantages of the present invention include provision of an easily modifiable device for fitting to a MRA. This means that the device may be provided as an off-the-shelf kit for patient use or be fitted by a clinician. The devices are easily modified for different patients as well are easily modifiable for the changing needs in a single patient. Further any changes required to the degree of mandibular protrusion and/or movement of the mandible can easily be made by the patient or clinician without the need to send the device to the laboratory for alteration.

In particular interchangeable arms 240 provide varying protrusive positions and the fact that different length of slot 254 can be provided means that varying vertical mandibular movement (opening and closing) can be obtained. Further the height of spigot 233 in second attachment member 230 provides for varying degrees of lateral (side to side) movement. The combination of features means that when fitted a patient can rotate the mandible without retrusion allowing the patient to gain relief from any discomfort while still obtaining therapeutic benefit from the protrusive position in which MRA 100 retains the mandible.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Sections I & II of Australian innovation patent 201 51 01 689 which provide a guide to interpreting the present specification are herein incorporated by reference.

A description of an embodiment with several components or features does not imply that all or even any of such components/features are required. On the contrary, a variety of optional components are described to illustrate the wide variety of possible embodiments of the present invention(s). Unless otherwise specified explicitly, no component/feature is essential or required.

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

The invention claimed is:

1. A mandibular repositioning appliance including: a first splint with a first connecting member comprising a forward facing axis for protrusive positioning of a mandible: a second splint with a second connecting member; and a link arm coupled to said first connecting member for free pivotal movement about said forward facing axis, the link arm extending transverse to said forward facing axis along a transverse axis in a transverse dimension to engage with said second connecting member in a slidable coupling that allows a range of relative movement in said transverse dimension; wherein protrusive positioning of the mandible is provided by relative positioning of the link arm along said forward facing axis; wherein said first and second connecting members are each attached to lateral legs of said splints such that the forward facing axis is substantially aligned with either side of the mid-sagittal plane in use in a patient, and wherein the link arm allows for guided, simultaneous movement along the transverse axis and free pivoting movement about the forward facing axis.

2. The mandibular repositioning appliance of claim 1 wherein said forward facing axis is provided by a shaft disposed along said first connecting member.

3. The mandibular repositioning appliance of claim 2 wherein said shaft is removably mounted.

4. The mandibular repositioning appliance of claim 3 wherein said removably mounted shaft is axially aligned in receiving slots in said first connecting member.

5. The mandibular repositioning appliance of claim 1 wherein said link arm is advanceable along said forward facing axis via a screw thread.

6. The mandibular repositioning appliance of claim 2 wherein the link arm and the shaft are fixed in relation to each other.

7. The mandibular repositioning appliance of claim 6 wherein the link arm and shaft are integral.

8. The mandibular repositioning appliance of claim 1 wherein the link arm comprises a slot opening for coupling with said second attachment member.

9. The mandibular repositioning appliance of claim 8 wherein the length of the link arm and/or length of the slot opening may be varied to provide variable amounts of vertical movement for opening and closing the mandible when the device is in use.

10. The mandibular repositioning appliance of claim 1 wherein the second connecting member comprises a spigot, a height of which provides a variable amount of sideways or lateral movement of the mandible when the device is in use.

11. The mandibular repositioning appliance of claim 8 wherein ends of the slot opening are curved to facilitate rotation of the mandible when the device is in use.

12. The mandibular repositioning appliance of claim 1 comprising one set of a first connecting member, second connecting member and link arm disposed on said splints on one side of the midsagittal plane and another set of a first connecting member, second connecting member and link arm disposed on said splints on the other side of the mid-sagittal plane.

13. A method of retaining the mandible of a patient in a forward opening position for therapeutic purposes, said method comprising applying a suitably fitted appliance of claim 1 to a patient for an appropriate time.

14. A kit for making a readily adjustable mandibular appliance said kit including: upper and lower dental splints; at least one first connecting member attachable to one of said splints having a forward facing axis for protrusive positioning of the mandible: at least one second connecting member attachable to the other of said splints; wherein said first and second connecting members are attachable to lateral legs of said splints and the forward facing axis is substantially alignable with either side of the mid-sagittal plane in use in a patient; a series of interchangeable link arms, each of said link arms coupleable to the first connecting member for free pivotal movement about said forward facing axis such that the arm extends transverse to said forward facing axis along a transverse axis in a transverse dimension and is engageable with said second connecting member in a slidable coupling that allows in use a range of relative movement in said transverse dimension; wherein said link arms are positionable at varying points along the forward facing axis to provide variable protrusion of the mandible and/or said link arms are of varying length to provide variable opening and closing movement of the mandible in use, and wherein the link arms allow for guided, simultaneous movement along the transverse axis and free pivoting movement about the forward facing axis.

15. A system for providing a readily adjustable mandibular repositioning appliance, said system including:
   upper and lower dental splints;
   a first connecting member attachable to one of said splints having a forward facing axis for protrusive positioning of the mandible:
   a second connecting member attachable to the other of said splints;
   wherein said members are attachable to lateral legs of said splints such that the forward facing axis is substantially aligned with either side of the mid-sagittal plane in a patient; and
   a series of interchangeable link arms, each of said link arms mountable on the first connecting member for free pivotal movement about said forward facing axis such that the link arm extends transverse to said forward facing axis along a transverse axis in a transverse dimension and is engageable with said second connecting member in a slidable coupling that allows in use a range of relative movement in said transverse dimension; wherein said link arms are positionable at varying points along the axis to provide in use variable protrusion of the mandible and/or said link arms are of varying length to provide in use variable opening and closing movement of the mandible, and wherein the link arm allows for guided, simultaneous movement along the transverse axis and free pivoting movement about the forward facing axis.

16. The system of claim 15 wherein said forward facing axis is provided by a shaft.

17. The system of claim 16 wherein said link arms are advanceable along said forward facing axis via a screw thread.

18. The system of claim 16 wherein each link arm and the shaft are fixed in relation to each other.

19. The system of claim 18 wherein each link arm and shaft are integral.

20. The system of claim 15 wherein each link arm comprises a slot opening and ends of the slot opening are curved to facilitate rotation of the mandible when the device is in use.

21. A coupling device for use with a dental appliance for mandibular repositioning, including:
   a pivot mount adapted for lateral attachment to a first splint with a generally forward facing axis with respect to the user of the dental appliance when in use;
   a fixed mount adapted for lateral attachment to a second splint of the dental appliance; and
   a link arm coupled to the pivot mount for free pivotal movement about said forward facing axis, the link arm extending transverse to said forward facing axis along a transverse axis in a transverse dimension to engage with said fixed mount in a slideable coupling that allows a range of relative movement in said transverse dimension, wherein the link arm allows for guided, simultaneous movement along the transverse axis and free pivoting movement about the forward facing axis.

22. Use of the coupling device of claim 21 in a mandibular repositioning appliance:
   (i) to treat; alleviate and/or prevent snoring, sleep apnoea and other sleep disorders; certain types of temporal mandibular dysfunction or in temporal mandibular joint pain treatment;
   (ii) for orthodontic treatment;
   (iii) in post pharyngeal operations and examinations; or
   (iv) to retain the mandible in a forward opening position for other therapeutic purposes.

23. Use of the coupling device of claim 21 in the mandibular repositioning appliance:
   (i) to treat; alleviate and/or prevent snoring, sleep apnoea and other sleep disorders;
   certain types of temporal mandibular dysfunction or in temporal mandibular joint pain treatment;
   (ii) for orthodontic treatment;
   (iii) in post pharyngeal operations and examinations; or
   (iv) to retain the mandible in a forward opening position for other therapeutic purposes.

\* \* \* \* \*